(12) United States Patent
Black

(10) Patent No.: US 6,989,023 B2
(45) Date of Patent: Jan. 24, 2006

(54) HYGIENIC TREATMENTS OF BODY STRUCTURES

(75) Inventor: Michael Black, Foster City, CA (US)

(73) Assignee: Oralum, LLC, Foster City, CA (US)

( * ) Notice: Subject to any disclaimer, the term of this patent is extended or adjusted under 35 U.S.C. 154(b) by 196 days.

(21) Appl. No.: 10/616,367

(22) Filed: Jul. 8, 2003

(65) Prior Publication Data

US 2004/0006332 A1    Jan. 8, 2004

(51) Int. Cl.
*A61N 5/01* (2006.01)

(52) U.S. Cl. .......................................... 607/90; 607/88
(58) Field of Classification Search ............. 607/88–89
See application file for complete search history.

(56) References Cited

U.S. PATENT DOCUMENTS

| | | | | |
|---|---|---|---|---|
| 3,667,454 | A | 6/1972 | Prince ........................ | 128/24.2 |
| 4,779,173 | A | 10/1988 | Carr et al. ................... | 362/109 |
| 5,030,090 | A | 7/1991 | Maeda et al. ................. | 433/29 |
| 5,160,194 | A | 11/1992 | Feldman ...................... | 362/109 |
| 5,306,143 | A | 4/1994 | Levy ........................... | 433/29 |
| 5,401,171 | A | 3/1995 | Paghdiwala ................. | 433/215 |
| 5,611,793 | A | 3/1997 | Wilson et al. ................. | 606/2 |
| 5,658,148 | A | 8/1997 | Neuberger et al. .......... | 433/215 |
| 5,814,008 | A * | 9/1998 | Chen et al. ................... | 604/21 |
| 6,015,404 | A | 1/2000 | Altshuler et al. ............. | 606/9 |
| 6,026,828 | A | 2/2000 | Altshuler .................... | 132/311 |
| 6,056,548 | A | 5/2000 | Neuberger et al. .......... | 433/215 |
| 6,063,108 | A * | 5/2000 | Salansky et al. ............. | 607/89 |
| 6,080,146 | A | 6/2000 | Altshuler et al. ............. | 606/9 |
| 6,094,767 | A | 8/2000 | Iimura ......................... | 15/105 |
| 6,187,018 | B1 * | 2/2001 | Sanjay-Gopal et al. ..... | 606/130 |
| 6,202,242 | B1 | 3/2001 | Salmon et al. ............... | 15/22.1 |
| 6,238,425 | B1 * | 5/2001 | Thiberg ....................... | 607/89 |
| 6,273,884 | B1 | 8/2001 | Altshuler et al. ............. | 606/9 |
| 6,290,496 | B1 | 9/2001 | Azar ............................ | 433/29 |
| 6,485,300 | B1 | 11/2002 | Muller et al. ................ | 433/29 |
| 6,508,813 | B1 | 1/2003 | Altshuler ..................... | 606/9 |
| 6,511,475 | B1 | 1/2003 | Altshuler et al. ............. | 606/9 |
| 6,517,532 | B1 | 2/2003 | Altshuler et al. ............. | 606/9 |

(Continued)

FOREIGN PATENT DOCUMENTS

RU    WO 99/52596    10/1999

OTHER PUBLICATIONS

Belikov, et al., "Investigation of IR Absorption Spectra of Oral Cavity Bacteria," SPIE, vol. 2922, pp. 113-118.

(Continued)

*Primary Examiner*—Henry M Johnson, III
(74) *Attorney, Agent, or Firm*—Lumen Intellectual Property Services, Inc.

(57) ABSTRACT

Multiple hygienic effects are concurrently applied to body structures. This is established by two or more light source sources each capable of delivering a light beam to the body structures using an optical means whereby each light beam provides a unique hygienic effect to the body structures. The device could be a handheld device with detachable components. The device could also be a brush or a comb. The device could include a massaging means and/or a vibrating means. An agent could be used to the body structures to assist in the hygienic treatment plan. A cradle could be included to store the device, reload the power supply of the device, as well as a means to communicate with a hygienic service provider. The cradle could also host a displaying means and a selecting means.

13 Claims, 18 Drawing Sheets

U.S. PATENT DOCUMENTS

| | | | |
|---|---|---|---|
| 6,558,372 B1 | 5/2003 | Altshuler | 606/2 |
| 6,569,156 B1 | 5/2003 | Tankovich et al. | 606/10 |
| 6,613,042 B1 | 9/2003 | Tankovich et al. | 606/10 |
| 6,666,878 B2 | 12/2003 | Carlgren | 607/91 |
| 6,758,844 B2 | 7/2004 | Neuberger | 606/3 |
| 6,860,896 B2 * | 3/2005 | Leber et al. | 607/88 |
| 6,866,395 B2 * | 3/2005 | Phipps et al. | 362/198 |
| 6,866,678 B2 * | 3/2005 | Shenderova et al. | 607/88 |
| 6,923,762 B1 * | 8/2005 | Creaghan, Jr. | 600/249 |
| 2002/0001202 A1 * | 1/2002 | Williams et al. | 362/572 |
| 2002/0128635 A1 | 9/2002 | Altshuler et al. | |
| 2002/0173780 A1 | 11/2002 | Altshuler et al. | |
| 2003/0055413 A1 | 3/2003 | Altshuler et al. | |
| 2003/0055414 A1 | 3/2003 | Altshuler et al. | |
| 2003/0065314 A1 | 4/2003 | Altshuler et al. | |
| 2003/0093915 A1 | 5/2003 | Pearl et al. | 34/96 |
| 2004/0044384 A1 * | 3/2004 | Leber et al. | 607/88 |
| 2004/0049247 A1 | 3/2004 | Perricone | 607/88 |
| 2004/0077977 A1 * | 4/2004 | Ella et al. | 601/6 |
| 2004/0193235 A1 * | 9/2004 | Altshuler et al. | 607/88 |
| 2004/0193236 A1 | 9/2004 | Altshuler et al. | 607/88 |
| 2004/0210277 A1 * | 10/2004 | Becker et al. | 607/88 |

OTHER PUBLICATIONS

"Everything for Love the Tingler, Head Massager," www.drugstore.com.

http://www.karna-ddscomfordent.com/basics.html, "Basics of the Biolase Millennium Hydrokinetic (HKS) Hard/Soft Tissue Laser and Clinical Cases.".

http://www.igiaonline.com/iglaztootwhi.html, "IGIA Lazer-White Tooth Whitening.".

GA Askaryan, "The Biological Media," Kvantovaya Electronika, V9(N7):1370-1383).

* cited by examiner

Figure 3
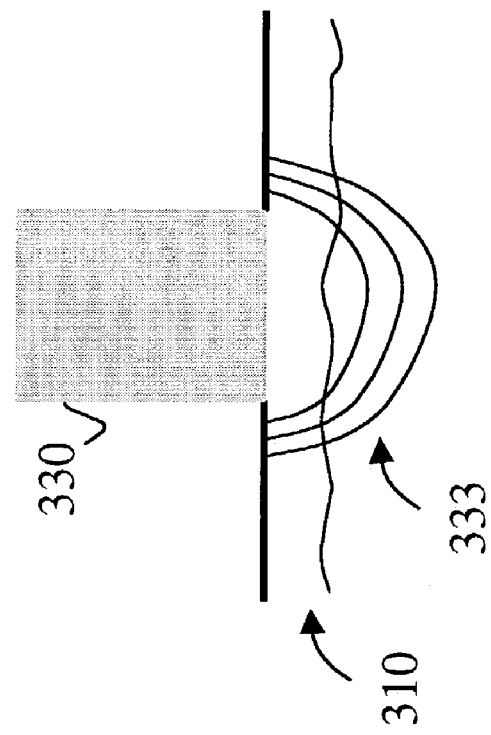
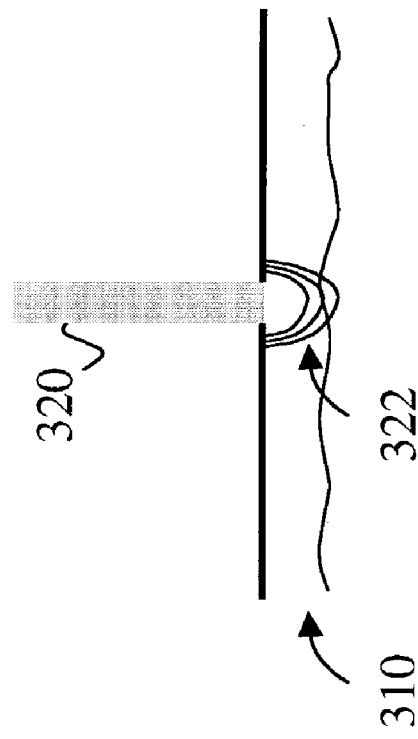

HYGIENIC TREATMENTS OF BODY STRUCTURES

FIELD OF THE INVENTION

This invention relates generally to hygienic devices, methods and systems. More particularly, the present invention relates to the application of hygienic effects at body structures.

BACKGROUND

Hygiene relates to the principles of cleanliness, promotion and preservation of health or the freeing from disease-causing microorganisms. Hygienic effects can be established in different ways of which one is through the effect of light on biological structures. For instance, the hygienic effect of visible, near ultraviolet and infrared light on biological structures is well known and has been described to provide anti-inflammatory effects, preventative effects, anti-bacterial effects, sterilizing effects, cleaning effects, cosmetic effects, therapeutic effects, healing effects (bio-stimulative effects), bio-altering effects, pain-releaving effects, agent-penetrating effects, photo-rejunivating effects and photo-dynamic treatment effects (See for instance a book by Goldman (1981) entitled "*The biomedical laser: technology and clinical applications*" and published by Springer-Verlag, New York; a book by Katzir (1993) entitled "*Lasers and optical fibers in medicine*" and published by Academic Press, New York; a book by Hajder et al. (1994) entitled "*Acupuncture and lasers*" and published by Ming, Belgrade; a book by Tuner et al. (1996) entitled "*Laser therapy in dentistry and medicine*" and published by Prisma Books, Grangesberg, Sweden; a book by Alster et al. (1996) entitled "*Cosmetic laser surgery*" and published by Wiley & Sons, New York; or a book by Fitzpatrick et al. (2000) entitled "*Cosmetic Laser Surgery*" and published by Mosby, St. Louis). The effects of a laser on biological structures is dependent on the laser properties (active matter, beam wavelength, continuous or impulse mode of operation), characteristics of the structures, water content, pigmentation degree, vascularization, vitality, heterogeneity, specific heat conductivity or time exposure. The photo-effect of a laser can be applied to superficial structures and subcutaneous structures. As far as the mechanisms of laser radiation effects are concerned, they may be thermal, mechanical or chemical.

When it comes to hygiene of the body, the art teaches a wide variety of toothbrushes that include a light source aimed at providing a hygienic effect to the oral cavity, e.g. gums and teeth. However, there is a need for devices typically used for the skin, hair or nails (e.g. brushes or combs) that include a light source aimed at providing a hygienic effect to the skin, hair or nails. The toothbrushes typically include a brush head and a light source. The light source illuminates through the bristles utilizing a certain transparency of the bristles or adjacent to the bristles. Even though these toothbrushes have the best of intentions by adding a hygienic effect to the daily exercise of tooth brushing, they cannot guarantee that the hygienic effect is actually applied to the gums or teeth. For instance, the use of toothpaste would partially or sometimes completely obstruct the penetration of the light beam, which would make the actual application of the light beam to the gums or teeth unknown and unreliable. If one assumes that the hygienic effect could in fact be reliably applied, then the current toothbrushes are still restricted to one single hygienic effect by selecting one light source that delivers radiation at one wavelength for each toothbrush. Unfortunately, the use of a single toothbrush that provides a single hygienic effect would not satisfy a much more inclusive hygienic maintenance of an oral cavity in which multiple hygienic effects would be desired. Accordingly, there is a need to provide new hygienic devices and methods that would satisfy a much more inclusive application of multiple hygienic effects for body structures such as skin, hair and nails, and their underlying structures.

SUMMARY OF THE INVENTION

The present invention overcomes the shortcomings in the prior art by providing a device and method capable of applying hygienic effects to body structures. This is established by two or more light sources each capable of delivering a light beam to body structures whereby each light beam provides a unique hygienic effect to the body structures. The preferred light source is a low power light source, including light emitting diodes or semiconductor lasers, capable of delivering light from the ultraviolet, visible or infrared spectrum. An optical path is used for each light beam to apply the light beam to the body structures. The optical path could include one or more optical components such as optical fibers, lenses, spectral filters, mirrors, transparent materials, semi-transparent materials, prisms, reflective coatings, reflecting grooves, beam splitters, collimators, light channels or gratings.

Dependent on the type of body structure various kinds of hygienic effects can be selected such as, but not limited to, an anti-inflammatory effect, a preventative effect (e.g. disease, irritation or the like), an anti-bacterial effect, a sterilizing effect, a cleaning effect, a cosmetic effect, a therapeutic effect, a healing effect, a bio-stimulative effect, a bio-altering effect, a pain-releaving effect, an agent penetrating effect, a photo-rejunivating effect, a photo-dynamic treatment effect, a skin stimulating effect, a hair growth stimulating effect or a nail treatment effect. In general, for the case of two more light sources, at least two of the same light sources could be used each delivering a unique hygienic effect or at least two different light sources could be used each delivering a unique hygienic effect. The desired hygienic effects that one would like to obtain guides the choice of light sources and its parameters. By varying parameters such as e.g. fluence, spot size, mode such as continuous or pulsed, repetition rate, pulse duration different hygienic effects could be established. The device could be used in a quasi-stationary manner or in a dynamic manner. In one aspect, the application of light beams at different locations to the body structures is established through movement of the device. Blending of different unique hygienic effects could be achieved at different locations of the body structure. Examples of body structures include skin, hair and/or nails. Body structures could include any type of microorganism (including disease-causing microorganisms), cell layers, tissues, organs or materials as well as any type of non-biological materials that are present at a body structure.

The device could further include a massaging means to massage the body structures and improve the transparency to the light beams. The device could also include a vibrating means to vibrate the body structures to provide additional or alternative massaging effects. Examples of a vibrating means include an ultrasonic means, a piezoelectric means or a mechanical means. The present invention could also include the application of an agent to the body structures before, during or after the application of the hygienic treatment. Examples of agents are, for instance, bioprotective agents, photocatalyst, treatment gels or cream, soothing agents, skin permeation enhancers or the like.

The device of the present invention could be a handheld device. In one aspect, the device could be a brush. In another aspect the device could be a comb. Furthermore, the device of the present invention could include several detachable components such as a detachable handle and a detachable head. The detachable head includes optical paths to generate and deliver the light beams to the structures. The head could be split up into at least two other detachable components. A first component that could include the light sources to generate the light beams and a second component that could include means to guide and output the light beams to the structures. All these components could be disposable components. A cradle could be included to store the device, reload the power supply of the device, as well as a means to communicate with a hygienic service provider and/or testing means. The cradle could also host a displaying means and a selecting means.

BRIEF DESCRIPTION OF THE FIGURES

The objectives and advantages of the present invention will be understood by reading the following detailed description in conjunction with the drawings, in which:

FIG. 3 shows an example of a fluence effect as a result of a small and a large light beam;

DETAILED DESCRIPTION OF THE INVENTION

Figure 1:
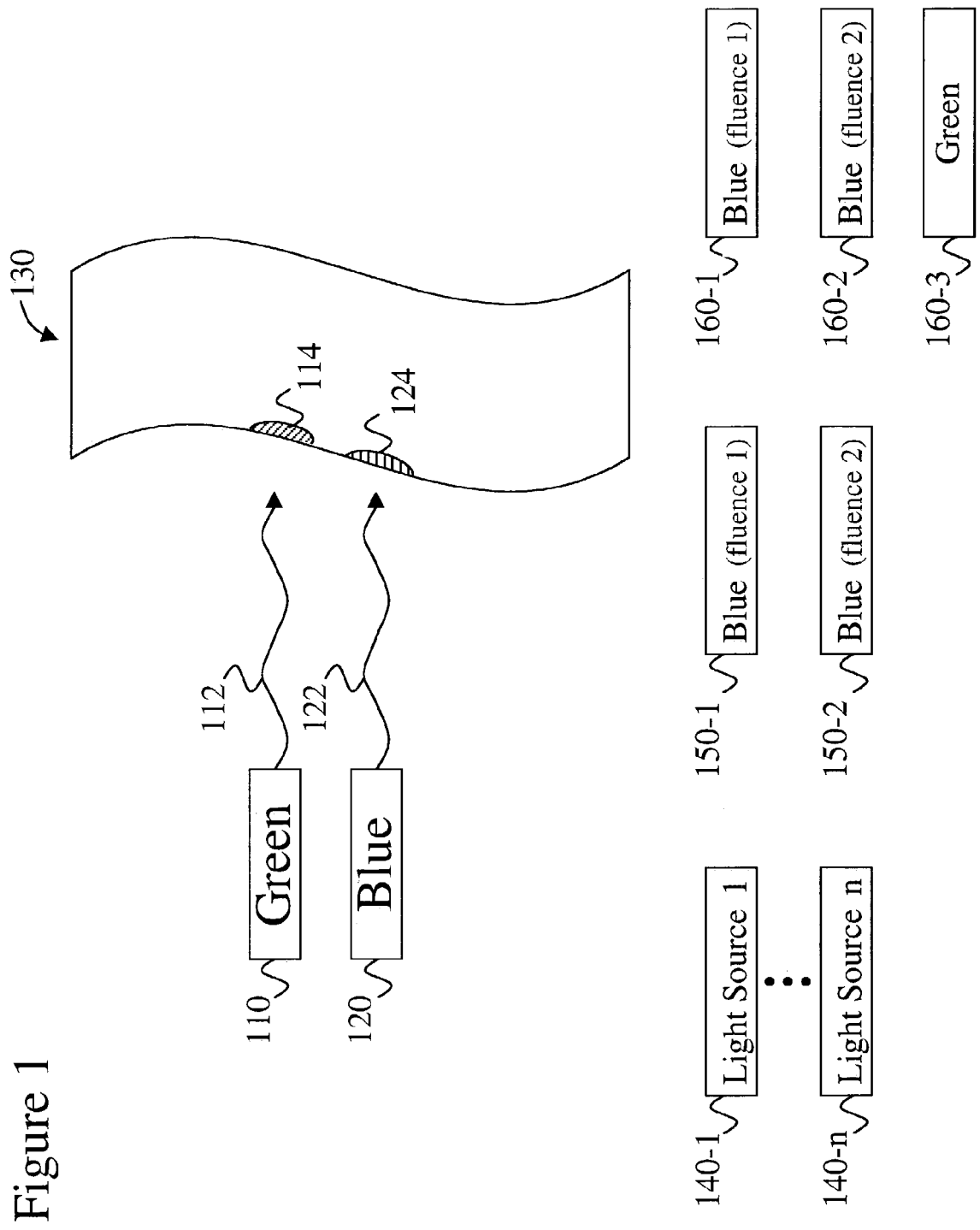
FIGS. 1–2 show examples of applying hygienic effects to body structures in a quasi-stationary manner according to the present invention.

Although the following detailed description contains many specifics for the purposes of illustration, anyone of ordinary skill in the art will readily appreciate that many variations and alterations to the following exemplary details are within the scope of the invention. Accordingly, the following preferred embodiment of the invention is set forth without any loss of generality to, and without imposing limitations upon, the claimed invention.

The present invention provides a device and method to apply hygienic effects at body structures. The hygienic effects are established by two or more light sources each capable of delivering a light beam with a unique hygienic effect at the body structures. The application of the hygienic effects could be established either in a quasi-stationary manner or a dynamic manner. The light sources are preferably low power light sources including low power lasers, light emitting diodes or low power semiconductor lasers (See, for instance, the following companies which are listed for purposes of illustration and should not be regarded as limiting to the invention: Coherent Inc., Santa Clara, Calif.; Microlasers by PolyScientfic Inc., Blackbury, VA; Photonic Products, Bishops Stortford, United Kingdom; Organic LEDs by Covion Organic Semiconductors GmbH, Frankfurt, Germany; Blue light emission from porous silicon by University of Science and Technology of China in Hefei). In general, for the case of two or more light sources, at least two of the same light sources could be used each delivering a unique hygienic effect or at least two different light sources could be used each delivering a unique hygienic effect. The desired hygienic effects that one would like to obtain guides the choice of light sources and its parameters. By varying parameters such as e.g. fluence, spot size, mode such as continuous or pulsed, repetition rate, pulse duration different hygienic effects could be established. A body structure is defined as any body structure that was created in a natural way, created in an unhealthy way or created in an unnatural way. Examples of naturally created body structures include the skin, hair and/or nails. Examples of an unhealthy created body structures are body structures that are caused by disease or infections. Examples of unnaturally created body structures are wounds, burns, or surgically created body structures. Body structures encompass any type of microorganism (including disease-causing microorganisms), cell layers, tissues, organs or materials as well as any type of non-biological materials that are present with a body structure.

In general, hygienic effects relate to the cleanliness of these structures, promotion and preservation of health of the structures or freeing the body structure from disease-causing microorganisms. In particular, the present invention encompasses hygienic effects related to the hygienic effect of visible, near ultraviolet and infrared light on these structures, which are known in the art (for a light spectrum refer to page 13 in a book by Tuner et al. (1996) entitled *"Laser therapy in dentistry and medicine"* and published by Prisma Books, Grangesberg, Sweden). Examples of such hygienic effects that could be selected as the two or more hygienic effects include anti-inflammatory effects, preventative effects (e.g. disease, irritation or the like), anti-bacterial effects, sterilizing effects, cleaning effects, cosmetic effects, therapeutic effects, healing effects (bio-stimulative effects), bio-altering effects, pain-releaving effects, photo-rejuvination effects, photodynamic effects, agent-penetration effects, a skin stimulating effect, a hair growth stimulating effect or a nail treatment effect.

To establish a particular hygienic effect at a body structure one needs to consider the light source properties such as the type of low power light source, wavelength of the light beam, the continuous or impulse mode of operation of the light sources, characteristics of the structures, water content of the structures, pigmentation degree of the structures, vascularization of the structures, vitality of the structures, heterogeneity of the structures, specific heat conductivity of the structures, the fluence of light penetration through a structure or the time exposure needed for the light beam. The art provides teachings on hygienic photo-effects of structures including guidelines regarding parameters such as the type of light source, selection of wavelength(s), fluence, penetration, selection of spot size, recommended pulse duration, recommended repetition rate, or the like. The selection of the hygienic effect(s) as part of the present invention incorporate these teachings as well as new teachings that become available in the art describing newly identified hygienic effects.

Currently available teachings are described in the following books, which provide an exemplary list rather than a comprehensive list. The list includes a book by Goldman (1981) entitled "*The biomedical laser: technology and clinical applications*" and published by Springer-Verlag, New York; a book by Katzir (1993) entitled "*Lasers and optical fibers in medicine*" and published by Academic Press, New York; a book by Hajder et al. (1994) entitled "*Acupuncture and lasers*" and published by Ming, Belgrade; a book by Tuner et al. (1996) entitled "*Laser therapy in dentistry and medicine*" and published by Prisma Books, Grangesberg, Sweden; a book by Alster et al. (1996) entitled "*Cosmetic laser surgery*" and published by Wiley & Sons, New York; or a book by Fitzpatrick et al. (2000) entitled "*Cosmetic Laser Surgery*" and published by Mosby, St. Louis).

FIG. 1 shows a first exemplary embodiment of two light sources 110, 120 delivering a light beam with a green wavelength 112 and a light beam with a blue wavelength 122, respectively. The green wavelength 112 and blue wavelength 122 each provide a unique hygienic effect when applied in a quasi-stationary manner to body structure 130. In this example, both light beams 112, 122 have a fairly superficial hygienic effect at body structure 130 as shown by 114, 124. In general, two or more light sources could be used such as n light source 140-1 to 140-*n*. As discussed supra, two of the same light sources could be used such as two light sources 150-1, 150-2 that each deliver blue light, however, with at least one different parameter to establish a different and unique hygienic effect for each of the two light sources 150-1, 150-2. Such as different and unique hygienic effect could be established by different fluences for each of the two light sources 150-1, 150-2, i.e. fluence 1 and fluence 2, respectively. Another examples is that there is one light source, e.g. 140-1 or 150-2, to deliver a hygienic effect. Yet another example is that there are three light sources, of which two are the same 160-1, 160-2 and one 160-3 is different, though all three delivering a unique hygienic effect.

Figure 2:
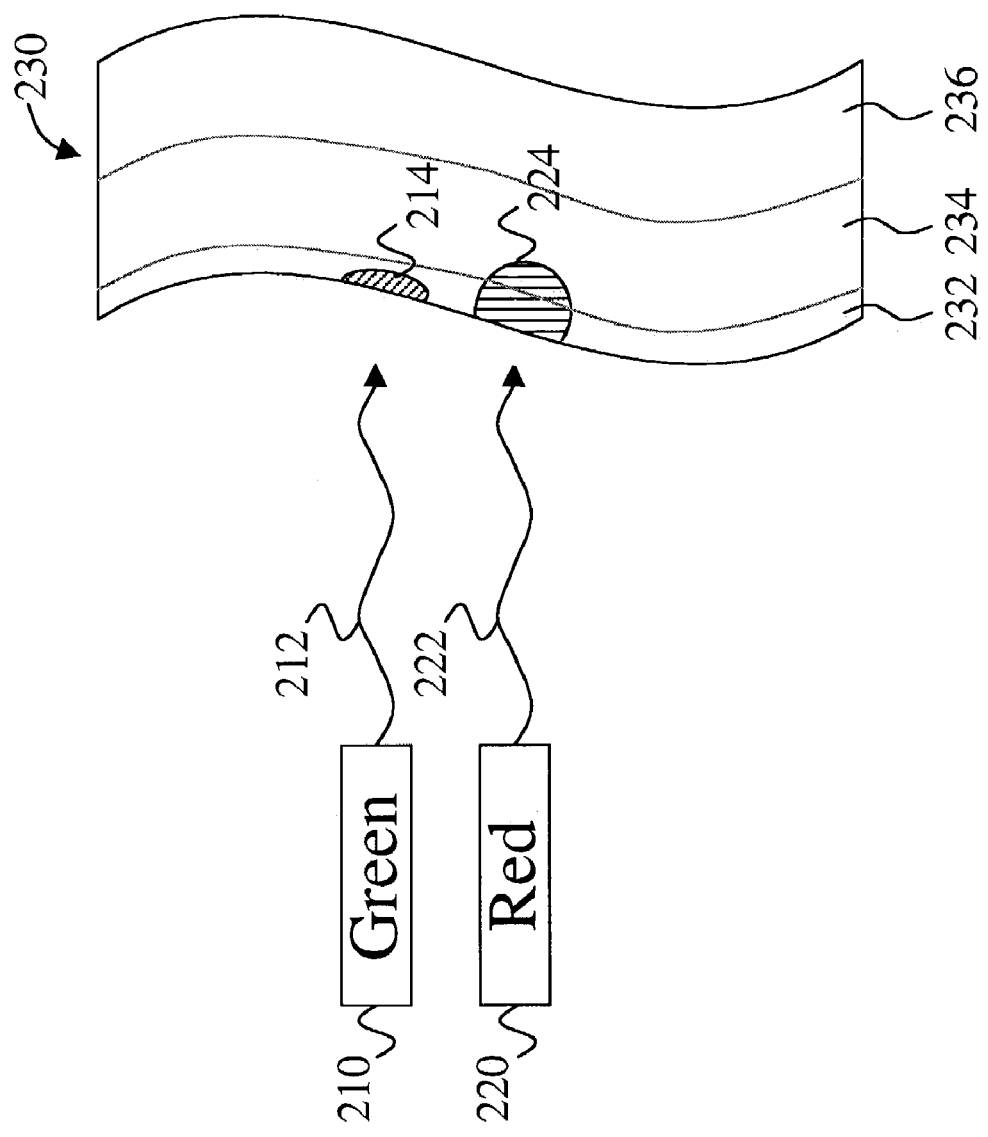

Body structure 130 is shown as a structure with a homogenous consistency. However, most structures that one would encounter, as described supra, have a heterogeneous consistency or formation. FIG. 2 shows a second exemplary embodiment of two light sources 210, 220 delivering in a quasi-stationary manner a light beam with a green wavelength 212 and a light beam with a red wavelength 222, respectively to a heterogeneous body structure 230. Structure 230 distinguishes three different layers, i.e. a superficial layer 232, a middle layer 234 and a deep layer 236. The green wavelength 212 and red wavelength 222 each provide a unique hygienic effect when applied at body structure 230. Light beam 212 has a superficial hygienic effect as shown by 214, which is similar to the example in FIG. 1. However, light beam 222 has a hygienic effect in superficial layer 232 that extends to part of middle layer 234. In other words, the red wavelength penetrates deeper in structure 230 than the green or blue wavelengths.

In addition, as it is known in the art, the relative subsurface fluence of a light beam in a structure 310 is dependent on the spot size, which could be relatively small 320 or relatively large 330, as shown in FIG. 3. The contour lines 322, 333 represent the relative subsurface fluences for identical fluences for the small 320 and large 330 spot size, respectively. The same subsurface fluence values appear at deeper levels with the larger 330 spot size compared to the smaller spot size 320.

Figure 4:
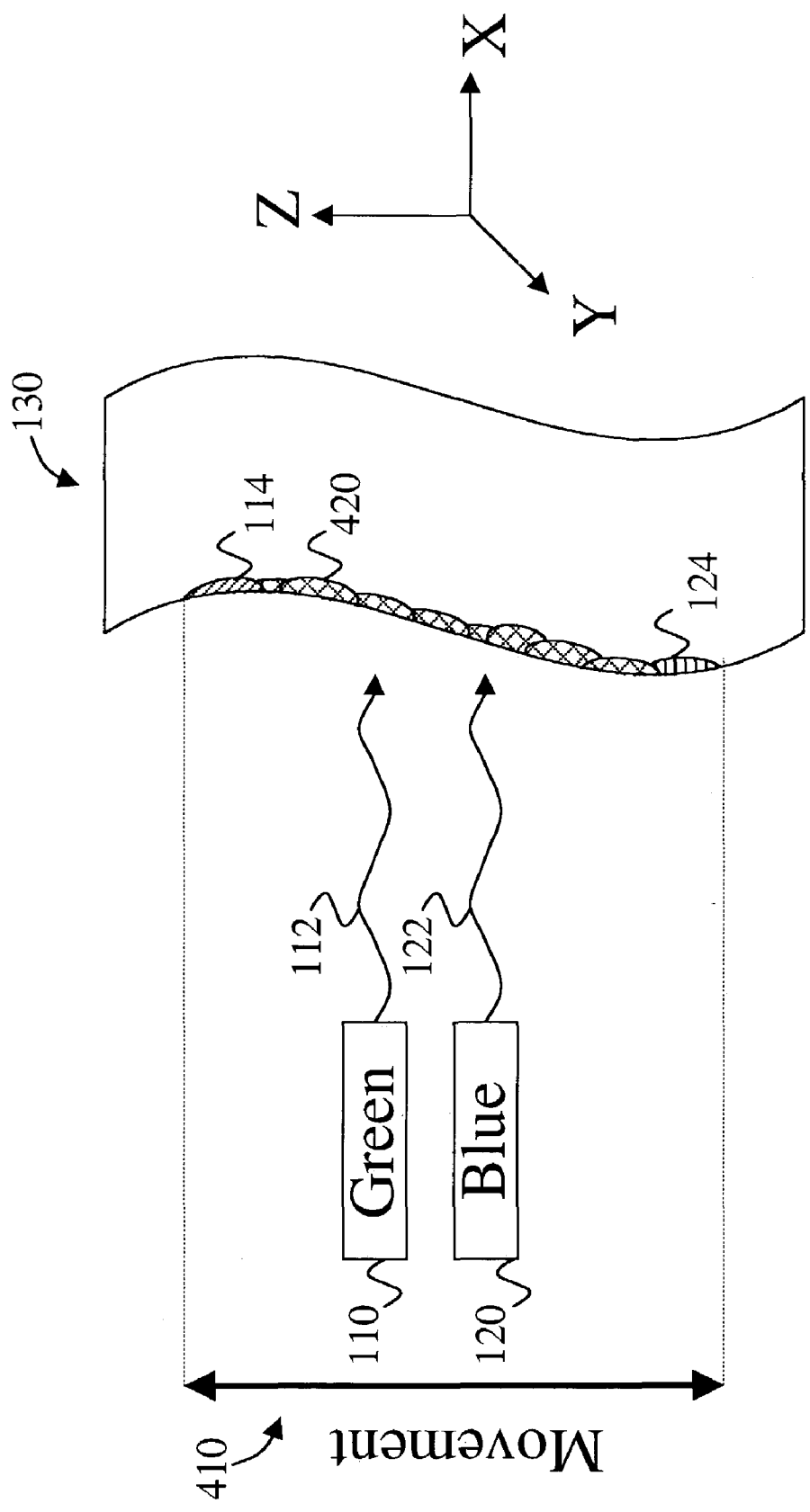
FIGS. 4–5 show examples of applying hygienic effects to body structures in a dynamic manner according to the present invention.
Figure 5:
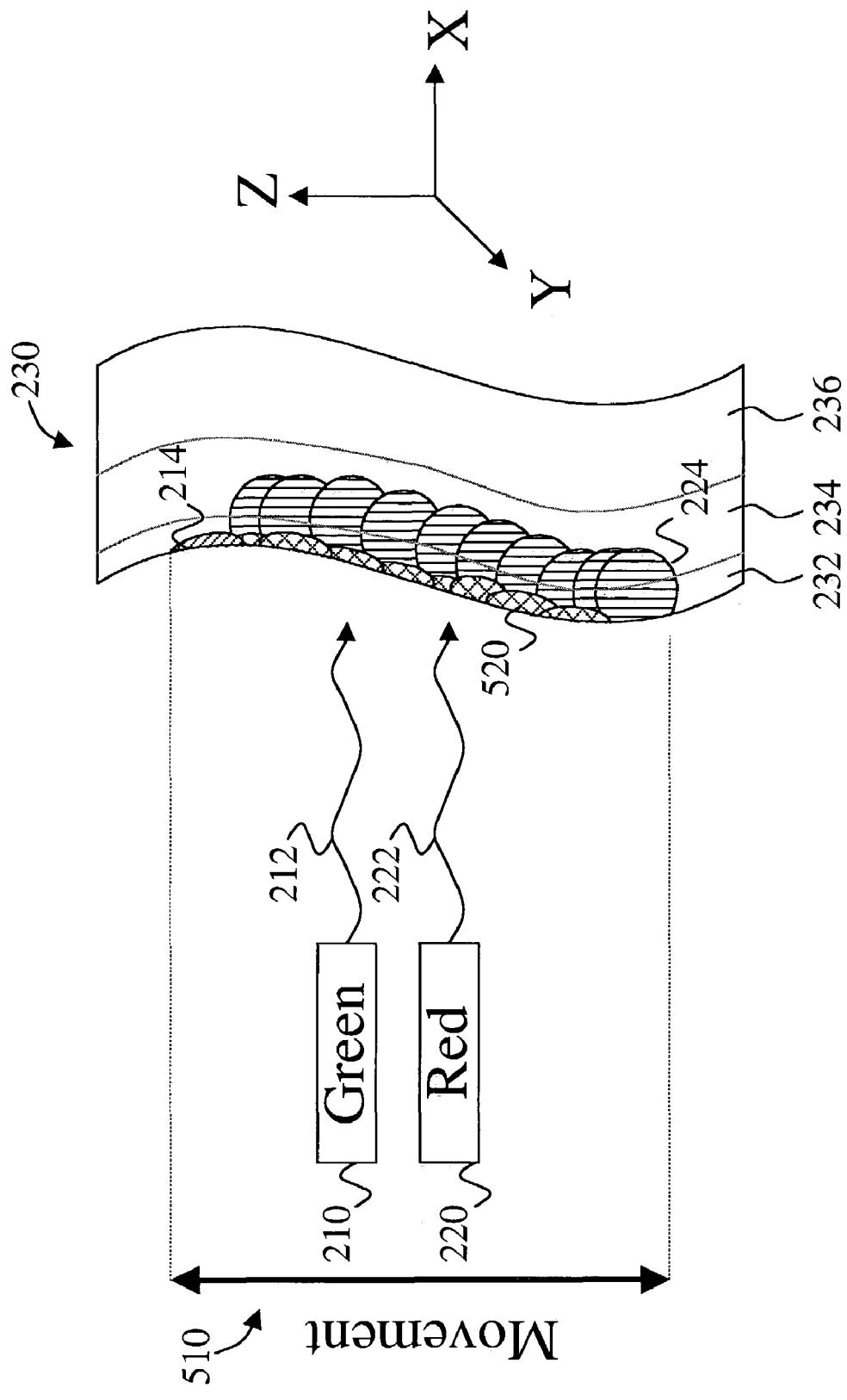

FIGS. 1–2 show exemplary embodiments of different hygienic effects in a body structure in which the light beams are applied in a quasi-stationary manner. FIGS. 4–5 show exemplary embodiments of the application of hygienic effects as shown respectively in FIGS. 1–2, but now in a dynamic manner. Movement 410 of light sources 110, 120 concurrently applies the hygienic effects 114, 124 to different locations at body structure 130 to achieve blending of these two unique hygienic effects at these different locations; 420 is an example of a blended hygienic effect of light beams 112, 124 as a result of movement 410, which is a blend of blue and green light. Movement 510 of light sources 210, 220 concurrently applies the hygienic effects 214, 224 to different locations at body structure 230 to achieve blending of these two unique hygienic effects at these different locations where some of the areas of penetration overlap; 520 is an example of a blended hygienic effect of light beams 212, 224 as a result of movement 510, which is a blend of red and green light. Note that there are areas where the hygienic effects do not blend together due to different penetration areas, though these hygienic effects are applied in a concurrent fashion. The movement relative to structure 130 is not limited to movement 410, 510 (i.e. Z translation), but could be applied in X, Y, or Z direction (translation/rotation).

Figure 6:
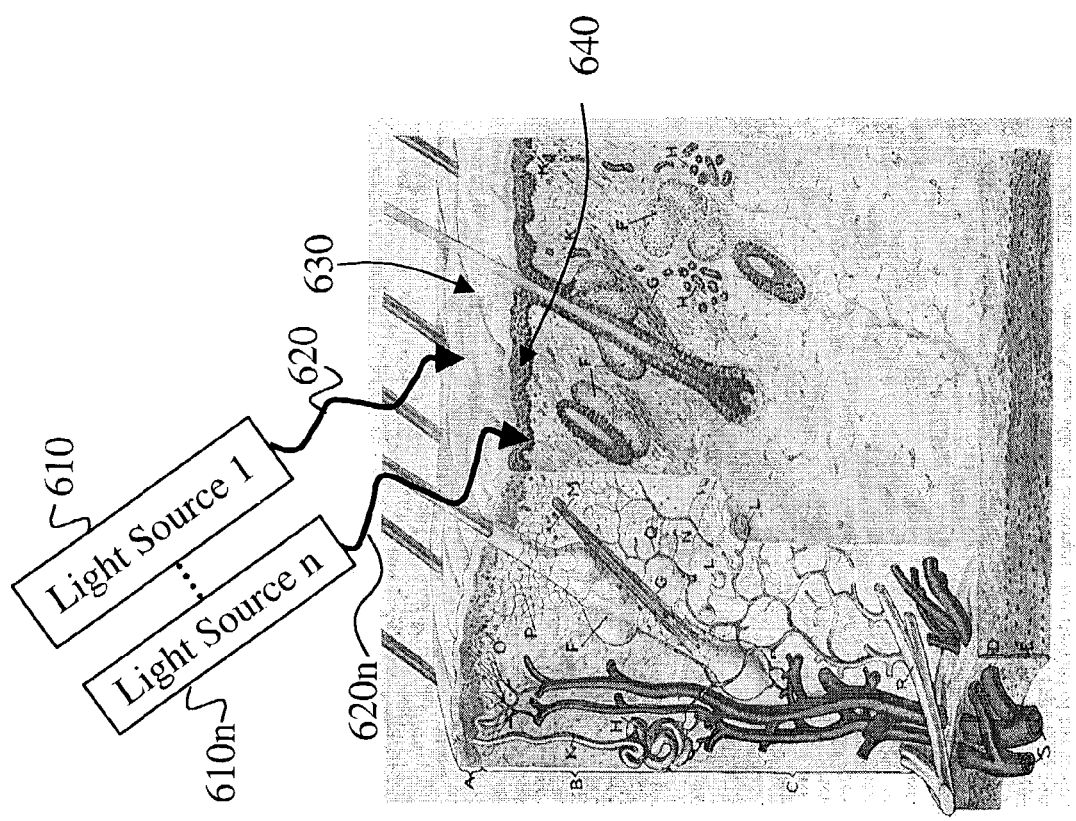
FIG. 6 shows an example of applying multiple hygienic effects to body structures according to the present invention.

FIG. 6 shows an exemplary embodiment related to the application of a plurality of light beams 610 . . . 610*n* produced by light sources 620 . . . 620*n*. On the one hand, light beam 610 could provide one or more hygienic effects focusing on the superficial skin layer 630 (epidermis) and could be selected as an anti-inflammatory effect, preventative effect, an anti-bacterial effect, a sterilizing effect, a cleaning effects, a therapeutic effect, a healing effect, a bio-stimulative effect, a bio-altering effect, a pain-releaving effect, a tissue rejuvenating effect, a photo-rejunivating effect, a photo-dynamic therapy effect and/or an agent penetrating effect. On the other hand, light beam 610*n* could provide one or more hygienic effects focusing on the subcutaneous skin layer 640 (e.g. dermis as indicated by arrow or deep fascia (not indicated by arrow), muscle (not indicated by arrow), etc.) and could be selected as, but not limited to, an agent penetrating effect, a preventative effect, a therapeutic effect, a healing effect, a bio-stimulative effect, a bio-altering effect, a pain-releaving effect, a tissue rejuvenating effect, a photo-rejunivating effect, and/or a photo-dynamic therapy effect. Again, as described supra, the application to the two skin layers could be accomplished in a quasi-stationary manner, but preferably in a dynamic manner more or less similar to the movements related to brushing.

Figure 7:
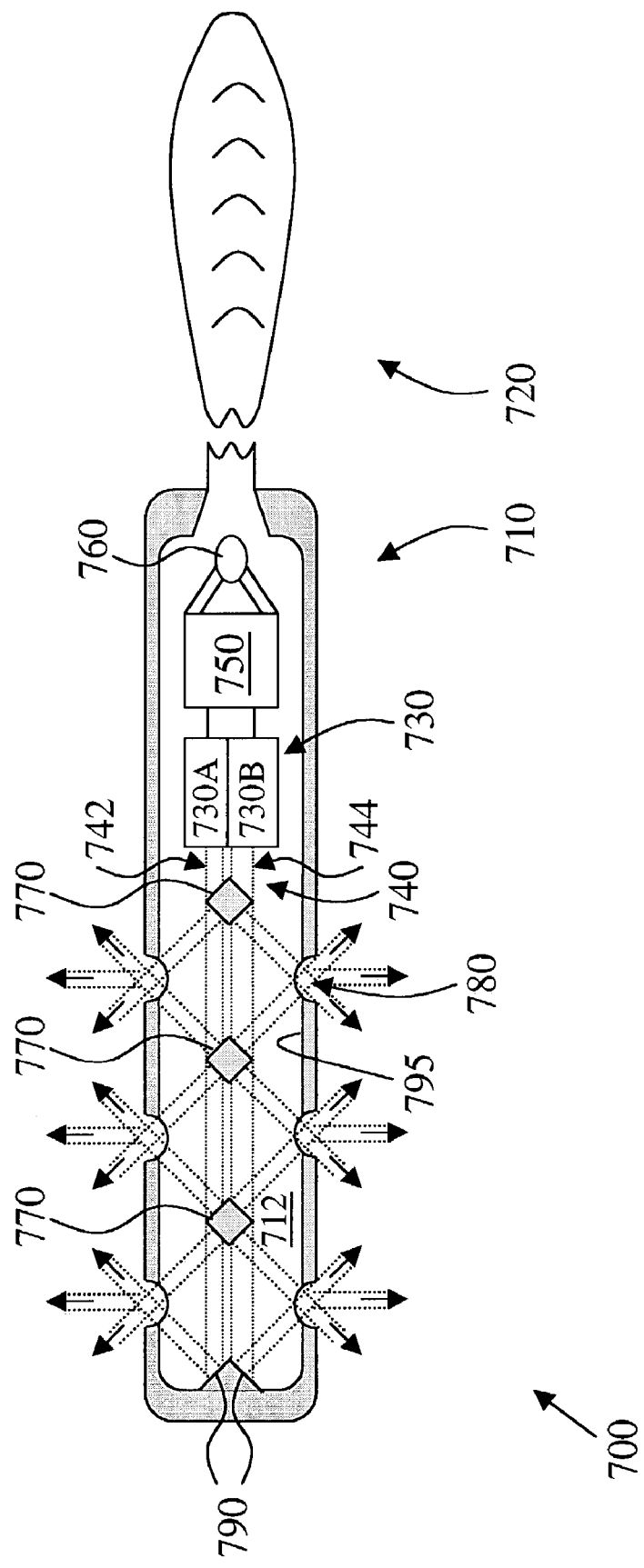
FIG. 7 shows an example of the device according to the present invention.

A first embodiment of a device of the present invention includes a head 710 and a handle 720 as shown by device 700 in FIG. 7. In one aspect, the handle and the head could be a single piece (not shown). However, in another aspect, as shown in FIG. 7, head 710 and handle 720 could be two separate parts of device 700, which would be preferred since it allows the user to replace the head with a new head or a different style head. The handle could take any shape and is not limited to the shape of handle 720 as shown in FIG. 7. However, it would be preferred to have an ergonomically shaped handle that easily fits in a user's hand. Different shapes and sizes of handles would then accommodate the shapes and sizes of the hands of children and adults. The inside 712 of head 710 includes light sources 730 (i.e. 730A, 730B) and deliver light beams 740 with the desired hygienic effect as discussed supra. For illustrative purposes it could be assumed that there are two light sources delivering a light beam 742 with a first hygienic effect and a light beam 744 with a second hygienic effect. However, as described supra the present invention is not limited to two light sources and could be one or more that two. Light sources 730 are powered by a power supply 750, such as a (rechargeable) battery. Power supply 750 is connected to a switch 760. Switch 760 is preferably positioned at the outside of head 720 and controls the on/off stage of power supply 750 and therewith the on/off stage of light sources 730. The present invention is not limited to one switch as there could also be multiple switches to control individual light sources or parameters. The inside 712 of head 720 includes an optical means with optical paths to direct light beams 742, 744 from the inside of head 720 to the outside of head 720. As a person of average skill in the art to which this invention pertains would readily appreciate, this could be accomplished in different ways. To accomplish the output of light beams 742, 744 one could establish different optical means or pathways, which could include one or more optical components. Examples of such optical components, which are commonly available in the art, include optical fibers, lenses, spectral filters, mirrors, transparent materials, semi-transparent materials, prisms, reflective coatings, reflecting grooves, beam splitters, collimators, light channels and gratings.

In the example of FIG. 7, the optical means includes reflective prisms 770 to reflect and direct light beams 742, 744 in such a way that they are able to pass through openings 780 as shown in FIG. 7 (note that for clarity only one opening is indicated by 780). Optical means could include a main reflective prism 790 at the end of the optical pathway in head 720 to further assist in outputting light beams 742, 744. Likewise, the optical means at the inside of head 720 could further include a reflective coating 795 to assist in outputting light beams 742, 744. Openings 780 could be considered as part of the optical means. Openings 780 could define a spot size. Openings 780 could also include one or more optical components such as a lens, a transparent material a semi-transparent material, or the like.

Figure 8:
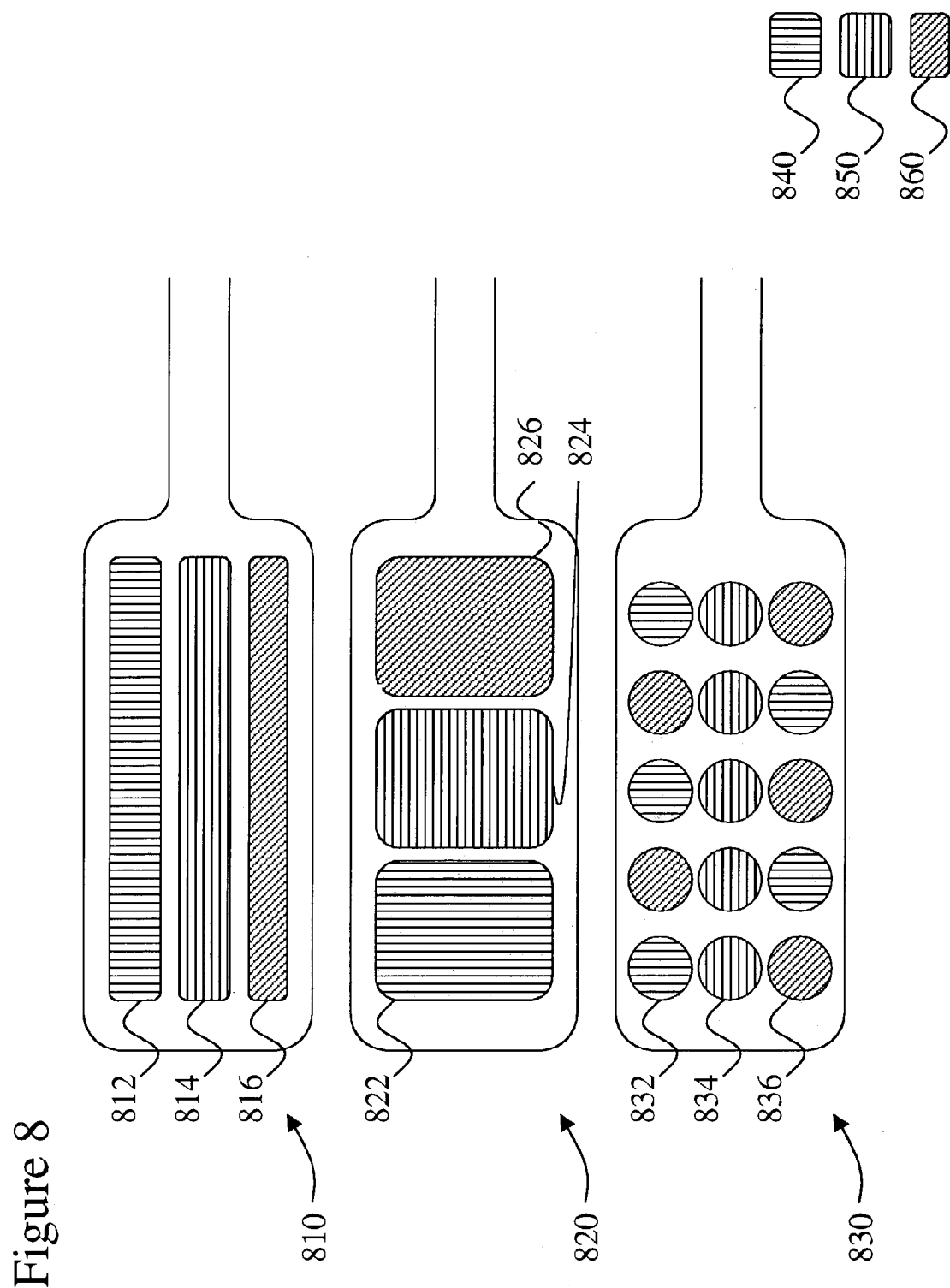
FIG. 8 shows examples of different configurations of the head of the device according to the present invention.

FIG. 8 shows different exemplary heads 810, 820 and 830 each with a different solution to outputting the light beams, which are shown for illustrative purpose only and should not be regarded as limiting to the invention. In the example of FIG. 8, three different hygienic light beams 840, 850, 850 are used. It is noted that the present invention is not limited to three different light beams, since it is also possible that one type of light beam, two different types of light beams or more than three different types of light beams can be used in the examples of FIG. 8. A first variation of the optical means could result in head 810 outputting light beams 840, 850, 850 through three rectangular shapes 812, 814, 816 distributed over head 810. Another variation of the optical means could result in head 820 outputting light beams 840, 850, 850 through three rectangular shapes 822, 824, 826 distributed over head 820. Yet another variation of the optical means could result in head 830 outputting light beams 840, 850, 850 through fifteen circular shapes 832, 834, 836 distributed over head 830 (note that only three circular shapes as indicated by 832, 834, 836 respectively). A consideration in the design of the optical outputs in a head relates to the ergonomics and ease of using the head when the hygienic effects are applied to a body structure.

Figure 9:
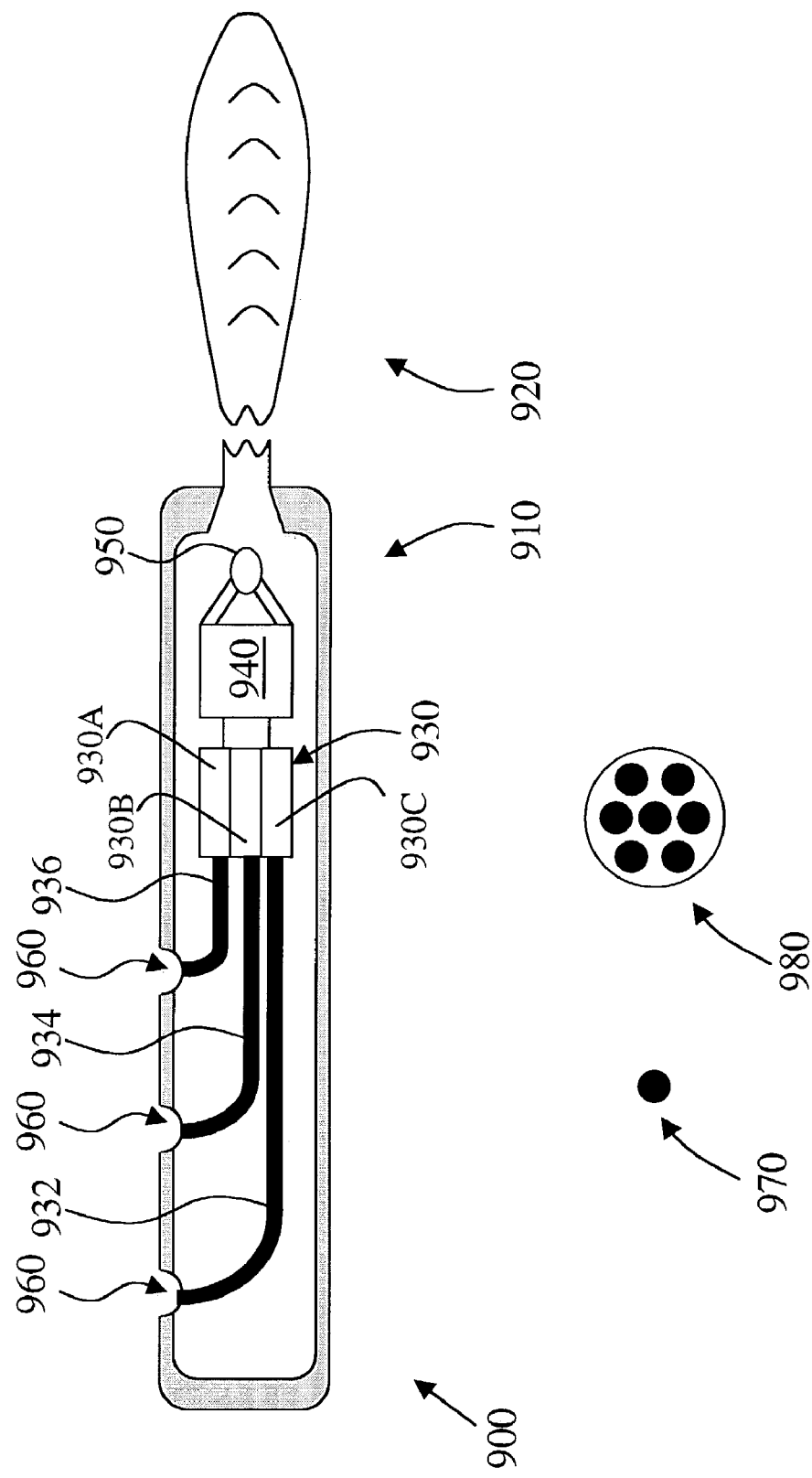
FIG. 9 shows another example of the device according to the present invention

A second embodiment of a device of the present invention is similar to device 700 as shown in FIG. 7 and is shown as device 900 in FIG. 9. Device 900 includes a head 910, handle 920, light sources 930 (i.e. 930A, 930B, 930C), power supply 940 and switch 950. The difference, however, between device 700 and device 900 is in the optical means. Device 900 includes optical fibers 932, 934, 936 that output the light beams from the light sources 930 through openings 960. In the example of device 900 there could be three light sources each delivering a light beam with a unique hygienic effect that is guided through optical fibers 932, 934, 936 respectively. There could be one optical fiber 960 connected to one opening or there could be several optical fibers bundled 970 together to output through one opening.

It has been shown that effect of radiation is improved in combination with massaging the gums. Pressuring alive soft tissue causes an increase in its transparacy thereby providing for better penetration of the radiation (See G A Askaryan (1982) in a paper entitled "*The increasing of transmission of laser and other radiation through the sift turbid physical and biological media*" and published in "*Kvantovaya Electronika*, V9(N7):1370–1383). The present invention generalizes this concept. Accordingly, the present invention could include a massaging means to massage the body structure(s) and improve the transparency to the light beams. A first aspect of applying a massaging effect relates to the movement of the head or the pressure of the head against the body structures will apply a massaging effect.

Figure 10:
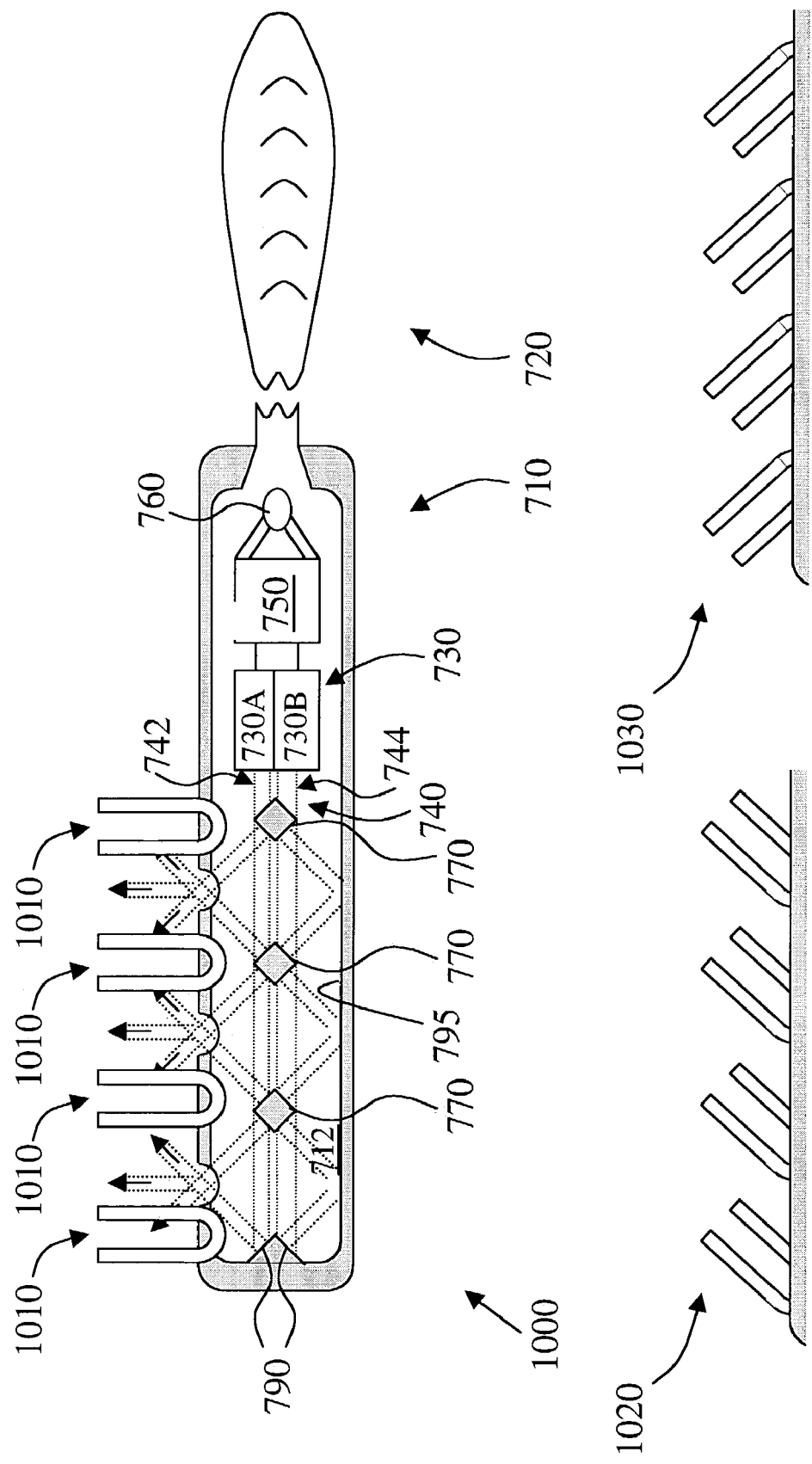
FIGS. 10–12 shows examples of the device with a brush according to the present invention.

FIG. 10 shows a second aspect of applying a massaging effect. Device 1000 is similar to device 700 with the difference of a massaging means 1010. Massaging means 1010 could be a brush or a comb. The bristles of the brush could be positioned in any direction with respect to the handle. For instance, bristles could be positioned more or less perpendicular to the head as shown by bristles 1010 or bristles could be positioned under an angle with respect to the head as shown by bristles 1020 and bristles 1030. The direction of the bristles could depend on the type or shape of the head or the type of massaging effect that would be desired. The type and size of bristles is dependent on the type of body structure. It would however be preferred to have flexible bristles that do not irritate or damage the structures. For instance, bristles could be made out of nylon, soft fiber, or any synthetic blend. The bristles could be attached to head 710 in a similar fashion as to how bristles are attached to a brush head or comb head. Massaging means is used in a similar fashion as a brush to add a massaging effect to the hygienic effect of the light sources. Device of the present invention could be a brush or a comb that provides hygienic effects according to the teachings of the present invention.

Figure 11:
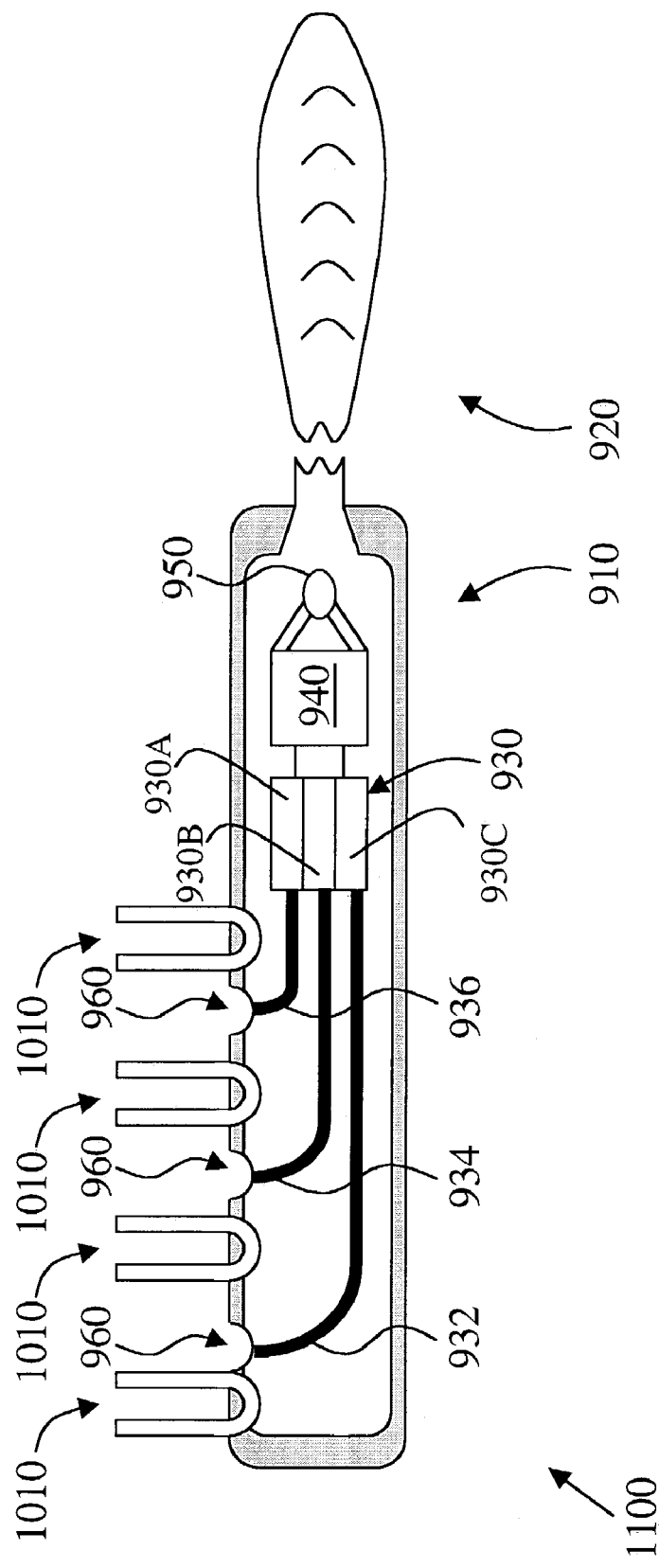
Figure 12:
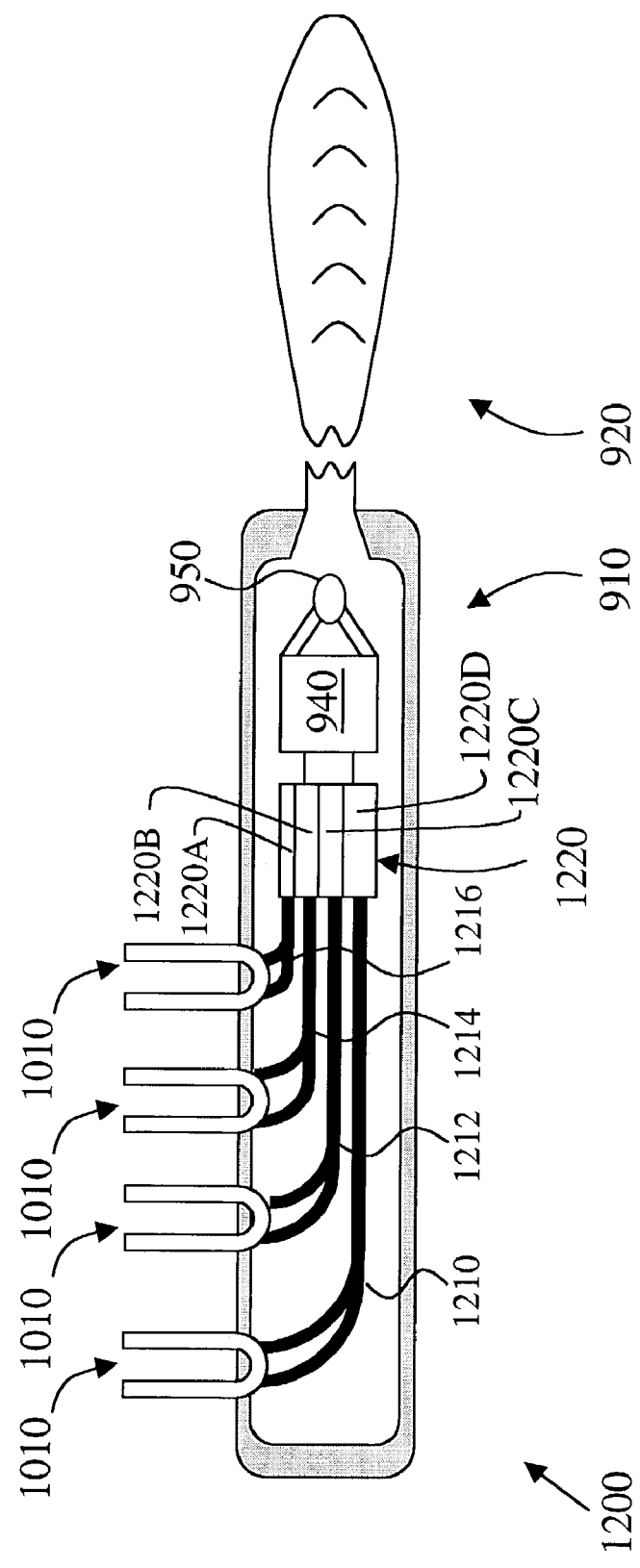

FIG. 11 shows a similar device 1100 as device 900 shown in FIG. 9 with the difference of the massaging means 1010. FIG. 12 shows device 1200, which is a variation of device 1100 as shown in FIG. 11. Device 1200 includes multiple optical fibers 1210 (2 fibers), 1212 (2 fibers), 1214 (2 fibers), 1216 (2 fibers) that transmit light beams from light source 1220 (including four light sources 1220A, 1220B, 1220C, 1220D). Another variation shown in FIG. 12 with respect to device 1100 is that the light beam does not pass through the openings 960 as shown in FIG. 9. Instead, an optical connection between the optical fibers and the bristles is created to establish that the bristles are able to continue to guide the light beams and finally output the light beams. In this case the bristles should be made out of materials capable of guiding light and flexible enough to prevent irritation or damage to the structures.

Figure 13:
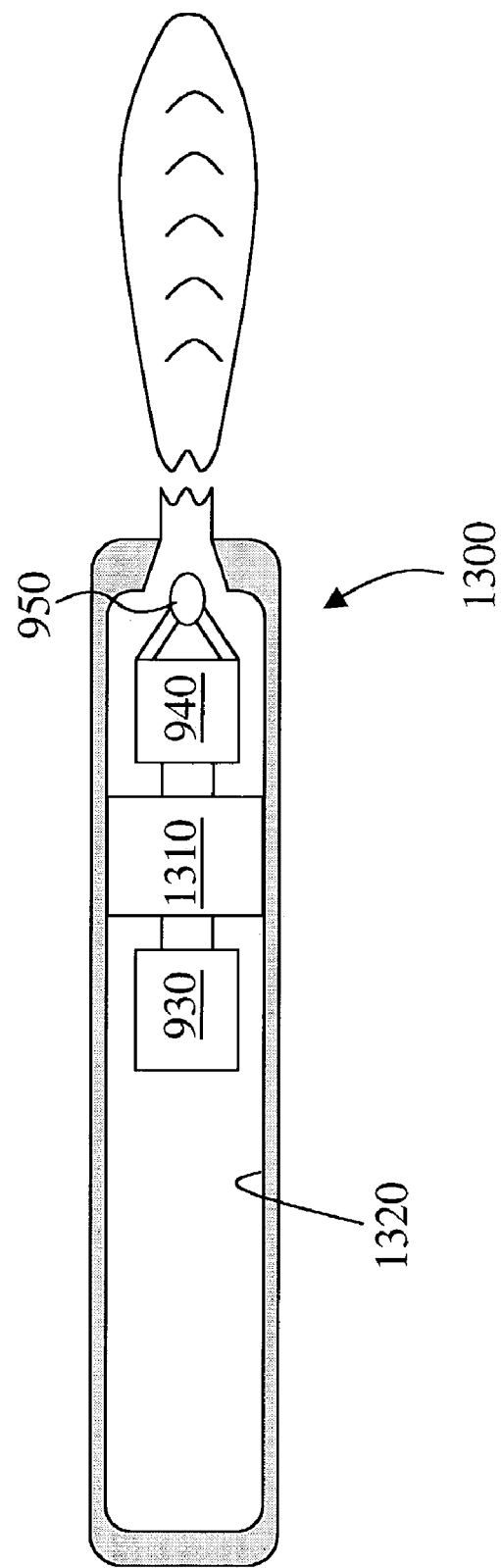
FIGS. 13–14 shows examples of the device with a vibrating means according to the present invention.
Figure 14:
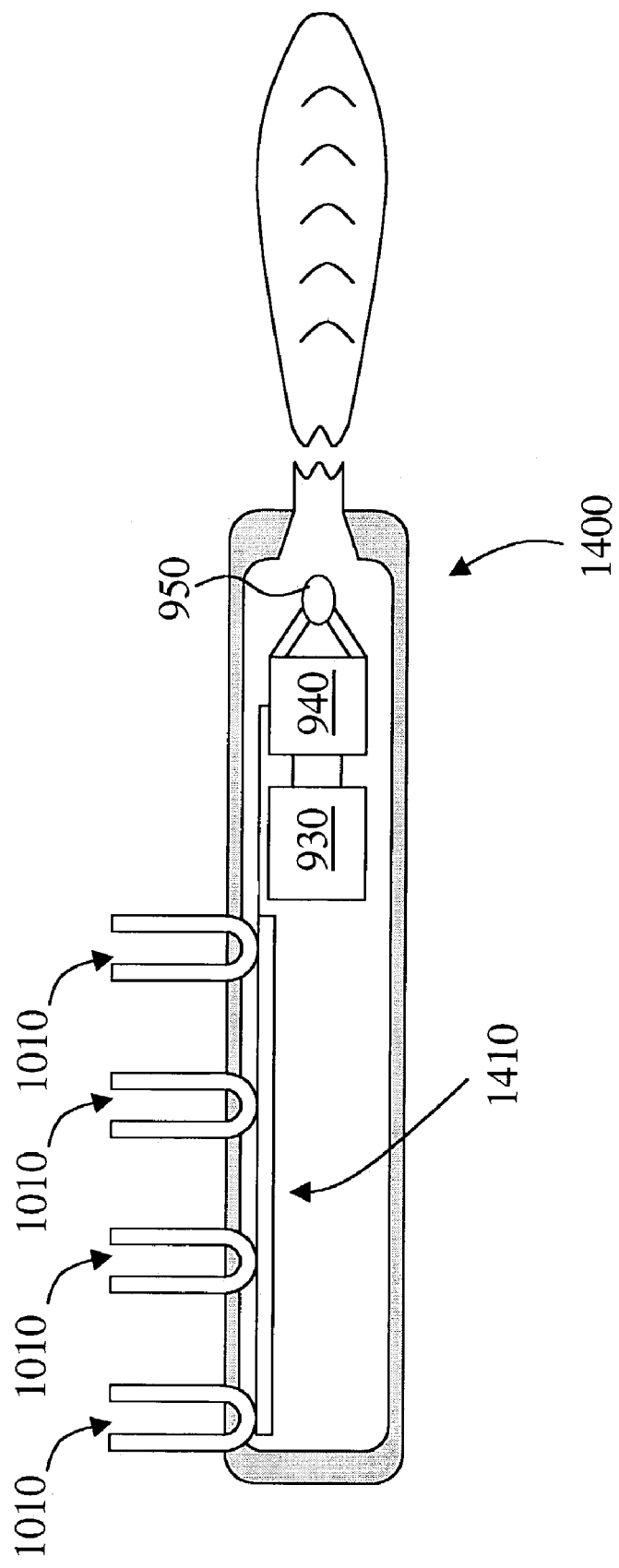

In another aspect, the present invention could include a vibrating means to vibrate the body structures and therewith provide an additional massaging effect. Examples of vibrating means that could be used are an ultrasonic means, a piezoelectric means or a mechanical means. Such vibrating means are known in the art. FIG. 13 shows a head 1300 with a vibrating means 1310. Since vibrating means 1310 is positioned against the inner edge 1320 of head 1300, the entire head 1300 might vibrate. FIG. 14 shows a head 1400 with a vibrating means 1410 that is connected in such a way to vibrate massaging means 1010, i.e. vibrating the bristles to provide an additional massaging effect to the massaging effect established by the bristles through movement as described supra.

Figure 15:
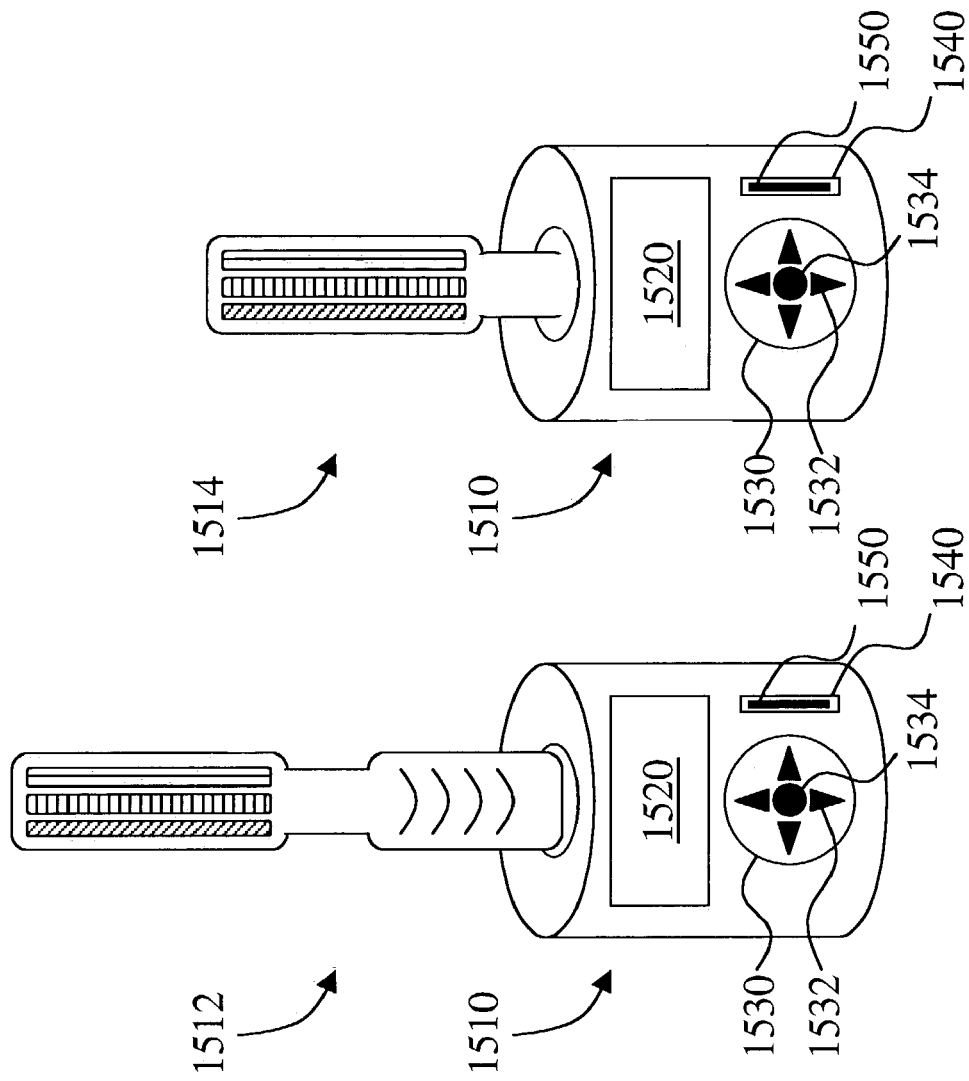
FIG. 15 shows the device in combination with a cradle according to the present invention.

FIG. 15 shows a cradle 1510 that can be used to store the hygienic device 1512 or the head 1514 of the hygienic device 1512. Cradle 1510 could also be used as a power supply (re)-charging device. In one aspect, hygienic device 1512 is placed in cradle 1510 and the power supply in the head is connected to a power recharging mechanism via the handle. In another aspect it would be possible to position the power supply of the hygienic device inside the handle, which is then directly connected to a power recharging mechanism. In yet another aspect, the head 1514 of the hygienic device is placed in cradle 1510 and the power supply in the head is directly connected to a power recharging mechanism.

Cradle 1510 could include a selection means 1540 for a user to select the hygienic effects or treatment parameters related to the unique hygienic effects. Selection means 1530 could be a selection means with, for instance, four arrow buttons 1532 and one center button 1534. Each arrow button 5132 corresponds to a function or selection that could be selected from a displaying means 1520. The up, down, left and right arrow buttons could relate to the browsing or selection from displaying means 1520. Displaying means 1520 could be any type or size of displaying means that would fit the cradle and is useful to the user. Necessary software and hardware components would be included to provide the functionality to display the parameters, selections and/or functions as well as provide functionality to the buttons. Center button 1534 could be used as the enter button to confirm a selection as is common in the art. The cradle could include different variations of a selection means and is not limited to the selection means shown by 1530.

Cradle 1510 could also include a slot 1540 for a read/writer card 1550 to read or write data. Examples of read/writer card 1550 are for instance a memory stick, compact flash card, smart media card, secure digital card, multi media card, microdrive or the like, which are common in the art. Read/writer card 1550 can upload information to the device, store information from the device, and could be interactively used with any type of hygienic service provider. A communication means such as a wireless protocol or Internet protocol could be included with the device to communicate with a hygienic service provider.

Figure 16:
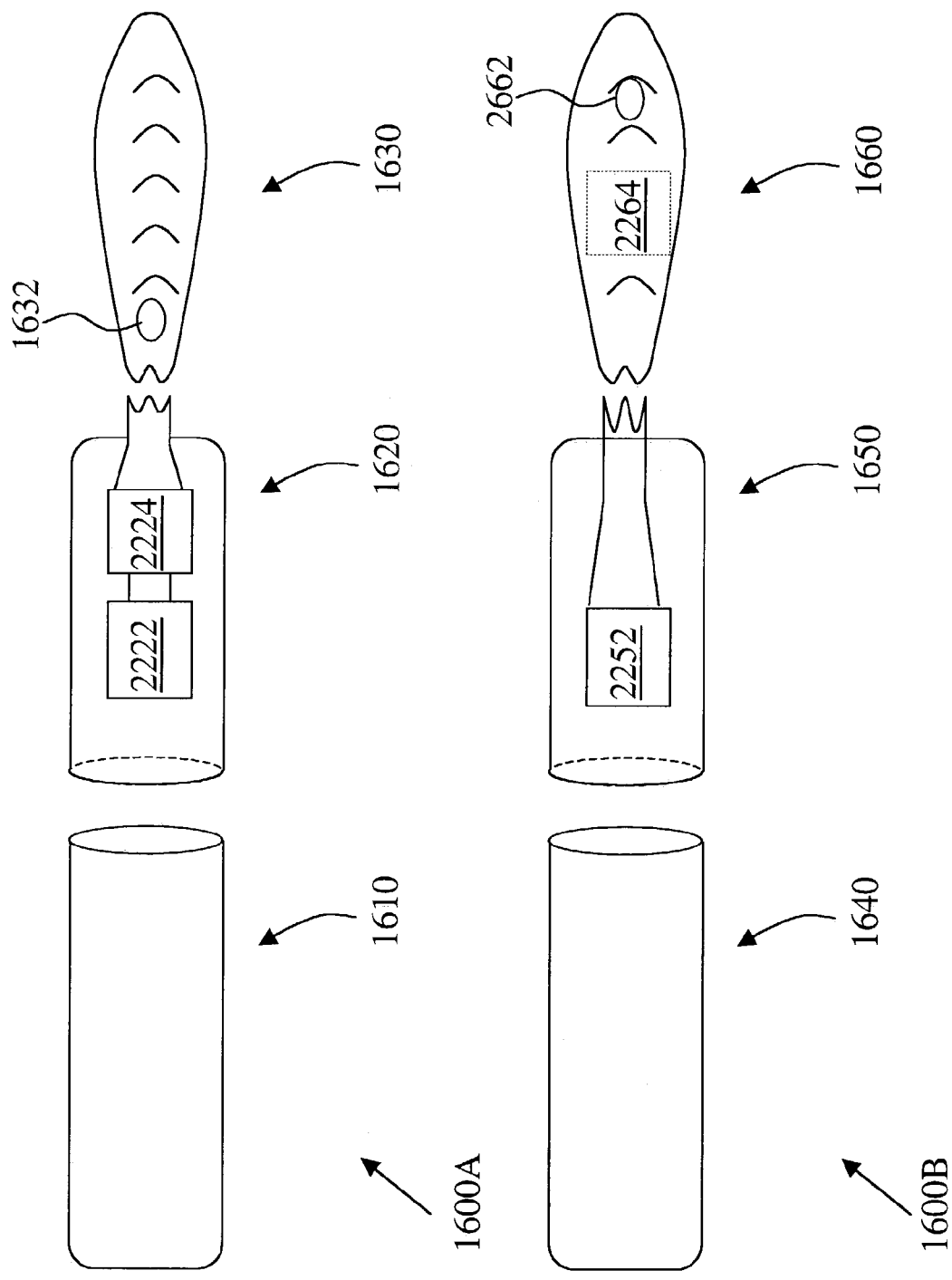
FIG. 16 shows detachable components of the device according to the present invention.

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For instance, the hygienic device of the present invention could be a handheld device. Furthermore, the hygienic device could have several removable or detachable components, which would allow these components to be changed, renewed or updated. For example, the components could be disposable components, or even recyclable components. FIG. 16 shows some examples 1600A, 1600B of configurations of detachable components of the hygienic device, which are shown for illustrative purposes only and should not be regarded as limiting to the invention. Device 1600A shows a head 1610 for optical guidance and output of the light beams, a mid-component 1620 hosting the light sources 1622 and the power supply 1624, and a handle 1630 with a switch 1632. Device 1600B shows a head 1640 for optical guidance and output of the light beams, a mid-component 1650 hosting the light sources 1652, and a handle 1660 with a switch 1662 and a power supply 1664. Another variation is that the device of the present invention could have pre-arranged settings or memory similar to car seat adjustment for individual users. This would allow different users to retrieve their personal settings by a simple click of a button or a simple voice command to the device.

Figure 17:
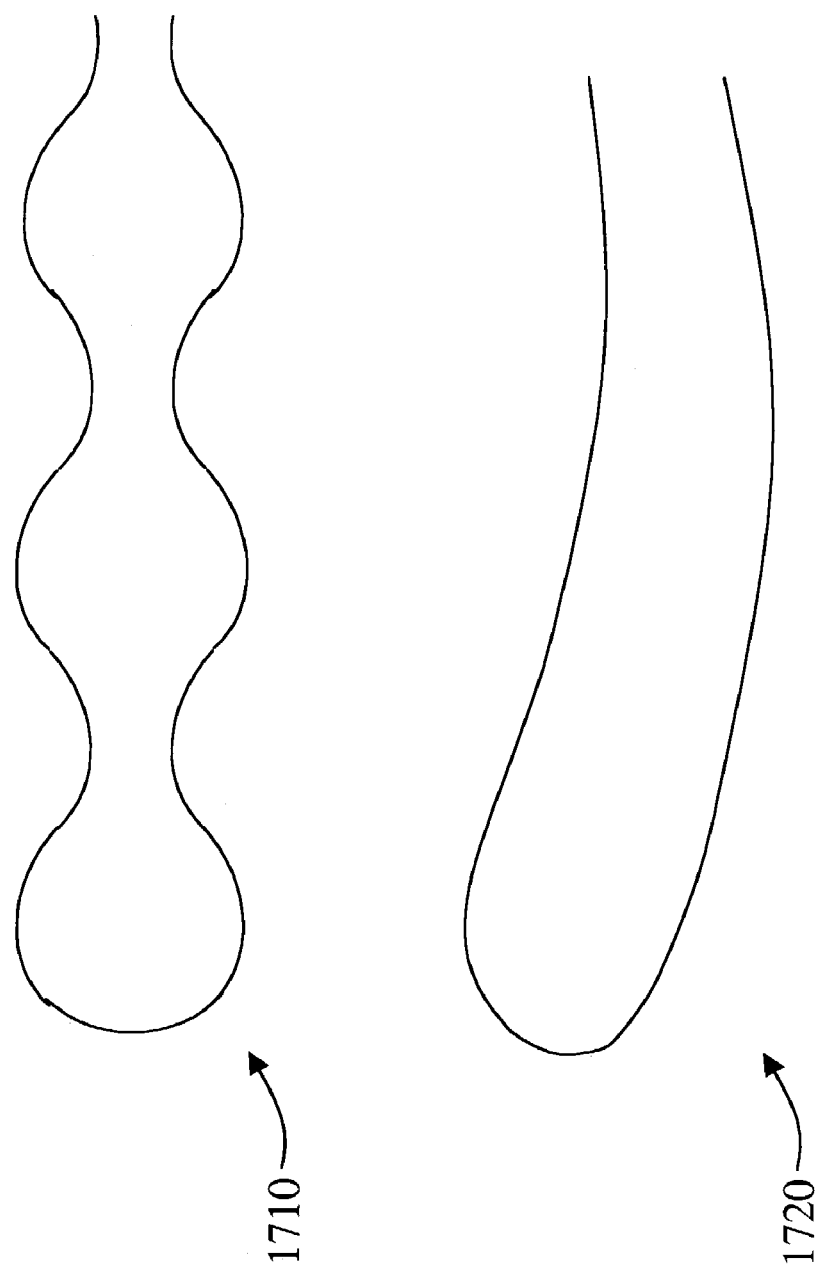
FIG. 17 shows different exemplary shapes of the head of the hygienic device according to the present invention.

Yet another variation to the hygienic device is the shape of the device; in particular the shape of the head component or the head and mid-components combined. FIG. 17 shows two examples of shapes that could be used, which are shown for illustrative purposes only and should not be regarded as limiting to the invention. Shape 1710 has an irregular but smooth surface that would for instance be desired to enhance the massaging effect or contribute to the output path of the light beams. Shape 1720 has a banana-like or curved shape and would for instance be desired to approach particular body structures that are difficult to access with a more rectangular shaped-component or device.

Figure 18:
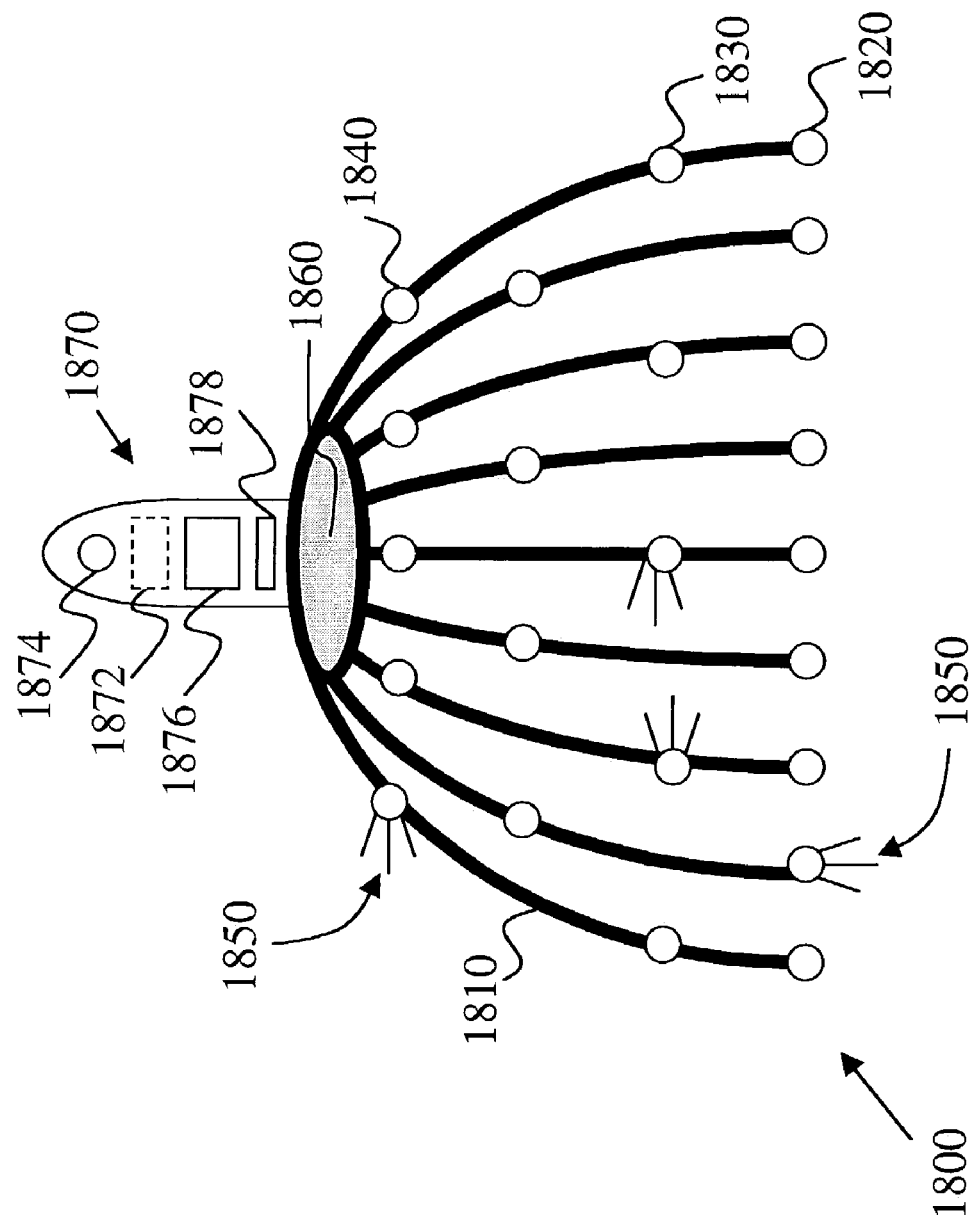
FIG. 18 shows an example of a variation of the massaging and/or vibrating means according to the present invention.

FIG. 18 shows still another variation of a device 1800 to apply hygienic effects. Device 1800 has multiple arms 1810 on which light sources 1820, 1830 and 1830 are attached. Light sources 1820, 1830 and 1830 could for instance be a blue, green and red light sources each providing, for instance, but not limited to, a different and unique hygienic effect. Again as discussed supra the type of light source and number of light sources can be varied and is dependent on the objectives of hygienic application(s). Light sources 1820, 1830 and 1830 could be placed at various different locations on arms 1810 and is not limited to the arrangement as shown in FIG. 18. The light 1850 that is outputted by each light source can also be delivered in different directions and is not limited to the directions shown in FIG. 18. Device 1800 could also include a massaging means and/or vibrating means 1860, which could provide additional vibration by similar massaging and/or vibration means as discussed supra. Massaging means and/or vibrating means 1860 could operate all arms 1810 simultaneously or one or more individual arms 1810 independently. Device 1800 include a hand piece 1870 that includes the light sources 1872 and one or more switches 1874. Optionally hand piece 1870 could include a display 1876 or a memory slot or communication means 1878.

Still another variation is to include pressure sensors with the device to control the pressure that is being applied to the body structures. The pressure sensors could provide feedback to the user about the amount of pressure or could provide feedback to a control system that controls the amount of pressure that is being applied.

Still another variation is that an agent could be used and applied to the body structures before, during or after the application of the hygienic treatment. Examples of agents are for instance bioprotective agents, photocatalyst, treatment gels or cream, soothing agents, skin permeation enhancers or the like (See, for instance, the following companies/products which are listed for purposes of illustration and should not be regarded as limiting to the invention: Neova by Procyte Corp. www.procyte.com; Medicalia Inc. www.medicalia.com; or ESBA Laboratories Inc.). Such agents could work as a catalyst, soother or enhancer to the structures. Still another variation relates to verifying the condition of the body structures before, during or after a hygienic treatment is applied. Such a diagnostics for structures could, for instance, be employed by means of spectroscopy resolved fluorescence (See e.g. Pferer et al., (2003) in a paper entitled *"Temporally and spectrally resolved fluorescence; spectroscopy for the detection of high grade dysplasia in Barrett's esophagus"* and published in *"Lasers in Surgery and Medicine* 32:10–16). Diagnostics of the structures could provide valuable information to evaluate and compare the efficacy of the hygienic treatment. All such variations are considered to be within the scope and spirit of the present invention as defined by the following claims and their legal equivalents.

What is claimed is:

1. A device to apply at a body structure one or more hygienic effects, comprising:
    (a) a handpiece; and
    (b) multiple arms, at least three, attached to said handpiece, wherein each of said multiple arms having distributed one or more light sources each capable of delivering a light beam at said body structure, wherein each of said light beams provides a unique hygienic effect at said body structure.

2. The device as set forth in claim 1, wherein said light sources are low power lasers, light emitting diodes or semiconductor lasers.

3. The device as set forth in claim 1, wherein said each of said light beams comprises light from the ultraviolet, visible or infrared spectrum.

4. The device as set forth in claim 1, further comprising an optical path for each of said light beams to individually apply each of said light beams to said body structure, wherein said optical path comprises one or more optical components wherein said one or more optical components are selected from the group consisting of optical fibers, lenses, spectral filters, mirrors, transparent materials, semi-transparent materials, prisms, reflective coatings, reflecting grooves, beam splitters, collimators, light channels and gratings.

5. The device as set forth in claim 1, wherein said handpiece further comprises a massaging means to massage said body structure through one or more of said multiple arms.

6. The device as set forth in claim 1, wherein said handpiece further comprises a vibrating means to vibrate said body structure through one or more of said multiple arms, wherein said vibrating means comprises an ultrasonic means, a piezoelectric means or a mechanical means.

7. The device as set forth in claim 1, further comprising a feedback means to provide feedback to a user over the pressure applied by one or more of said multiple arms to said body structure, wherein said feedback is selected from the group consisting of sound, display and vibration.

8. The device as set forth in claim 1, wherein said handpiece further comprises a selection means for a user to select parameters related to said unique hygienic effects or related to said light beams to a user.

9. The device as set forth in claim 1, wherein said handpiece further comprises a displaying means to display data related to said unique hygienic effects or related to said light beams to a user.

10. The device as set forth in claim 1, wherein said handpiece is a detachable handpiece.

11. The handheld device as set forth in claim 10, wherein said detachable handpiece comprises at least two detachable components, wherein a first component comprises said one or more light sources that generate said light beams and wherein a second component comprises means to guide and output said light beams to said body structure.

12. A handheld device to apply at a body structure one or more hygienic effects, comprising:
    (a) a handpiece; and
    (b) multiple arms, at least three, attached to said handpiece, wherein each of said multiple arms having distributed one or more light sources each capable of delivering a light beam to said body structure, wherein each of said light beams provides a unique hygienic effect based on a uniqueness in wavelength to said body structure.

13. A handheld device to apply at a body structure one or more hygienic effects, comprising:
    (b) a handpiece; and
    (b) multiple arms, at least three, attached to said handpiece, wherein each of said multiple arms having distributed one or more light sources each capable of delivering a light beam to said body structure, wherein each of said light beams provides a unique hygienic effect based on a uniqueness in fluence to said body structure.

* * * * *